United States Patent [19]
Hodges et al.

[11] 4,120,584
[45] Oct. 17, 1978

[54] METHOD OF PREPARING SMALL SAMPLES INCLUDING LINISHING AN AREA OF THE SAMPLES

[75] Inventors: Raymond John Hodges, Churchill; Charles Brian Belcher, Birmingham, both of Australia

[73] Assignee: Australian Wire Industries (Pty.) Limited, Melbourne, Australia

[21] Appl. No.: 701,178

[22] Filed: Jun. 30, 1976

[51] Int. Cl.² .............................................. G01N 1/00
[52] U.S. Cl. ...................................... 356/36; 29/407; 250/288; 250/460; 356/85; 356/244
[58] Field of Search ................. 250/288, 460; 356/36, 356/85, 86, 244; 29/407

[56] References Cited

U.S. PATENT DOCUMENTS

| 3,869,213 | 3/1975 | Greene | 356/244 |
| 3,901,599 | 8/1975 | Meric | 356/85 |
| 3,909,133 | 9/1975 | Hobson et al. | 356/86 |
| 3,992,114 | 11/1976 | Wade | 356/244 |

*Primary Examiner*—Vincent P. McGray
*Attorney, Agent, or Firm*—Murray & Whisenhunt

[57] ABSTRACT

A method of preparing small samples for analysis by instrumental techniques is disclosed, wherein the method includes steps of holding a representative plurality of samples in contact with a surface of a backing member, with said samples in close proximity to each other, and linishing or grinding an area of said samples across a surface parallel or tangential to said surface of said backing member.

13 Claims, 4 Drawing Figures

METHOD OF PREPARING SMALL SAMPLES INCLUDING LINISHING AN AREA OF THE SAMPLES

This invention relates to the preparation of samples for subsequent analysis by instrumental techniques and is particularly concerned with the analysis of wire samples in the size range that have a cross section area 0.1 to 100 mm$^2$. However, the invention applies equally to other forms of samples such as chips, scrapings, tubing, powder, filings, millings and turnings, and the method of preparation may be used with most instrumental methods of analysis, including optical emission spectroscopy (OES), X-ray fluoresence spectroscopy (XRF), mass spectrometry, ion microprobe, neutron activation, Mossbauer spectroscopy, Auger spectroscopy, electron spectroscopy, glow discharge spectroscopy, or X-ray diffraction.

Surface preparation of solid samples for instrumental analysis is necessary to achieve a sufficiently large and representative area of the sample in a suitable form to allow irradiation and excitation. Typical representative areas vary for each instrument, for example, OES generally requires a presentation area of about 15 mm in diameter whereas XRF is generally used on a presentation area of about 25 mm in diameter. Furthermore, the presentation area should be uniformly flat and free from physical imperfections. Without adequate preparation the analysis is not representative of the composition.

Conventional sample preparation techniques for instrumental analysis include: (1) remelting, (2) direct briquetting and (3) direct analysis of wire, linished on the ends.

The remelting techniques have disadvantages: a large mass is required to produce a remelted casting; there are losses of a number of important elements, and the time required for preparation is too long for routine plant operations.

The briquetting techniques also require a substantial sample mass and a high force to produce the required size briquette. The accuracy of the analysis is limited, inclusions cannot be held in a uniform orientation and cannot be related to solid standards, there are voids in the sample which disturb some techniques such as XRF where variable X-ray penetration can occur, whereas gas is evolved and the surface is distorted for the techniques that cause heating during excitation such as in OES.

Present published methods of chip analysis are confined to single pieces large enough to allow a complete excitation. For example, chips prepared on a large lathe are cut to 24 × 20 mm and pressed into reuseable lead or tin granules contained in a 25 mm aluminium cup. The method is satisfactory for OES with the large sample, although there are problems with cracks in the chip and with the aluminium. However, there is little or no deformation of the sample during pressing which precludes the use of wires or small chips as samples for analytical instruments. The technique fails for wire analysis and other small samples.

Wire samples greater than 2.5 mm in diameter are able to be analysed by direct methods using a jig to hold the end of a linished sample in the spark chamber, in place of the normal sample. There are claims that this technique is also suitable for some elements for wires with diameters as low as 1 mm if the wires are bunched together. Our experience has shown three inherent defects in this type of preparation for OES. (1) The samples overheat and give non-representative emission, e.g., a 1 mm wire will melt in 20 seconds. (2) The inclusions in the wire are oriented unfavourably for presentation to the arc, e.g. Mn and S emisison are generally biased high because of the orientation of inclusions formed during casting in the original ingot. (3) The accuracy of the analysis is restricted by the necessity of having standards of similar dimension and composition to the samples being analysed. (4) The precision of analysis of all elements is inferior to solid round samples and deteriorates rapidly for certain elements in wires in the size range 5–0.5 mm diameter. Furthermore, the area prepared is too small for other techniques such as XRF.

The object of this invention is to provide a method of preparation for rapid analysis of samples that are normally too small for direct irradiation and excitation by an instrument, while a more specific object is to provide a direct technique suitable for the complete range of sample sizes from the one calibration.

The invention therefore provides a method of preparing small samples for analysis by instrumental techniques comprising the steps of holding a representative plurality of samples in contact with a surface of a backing member with said samples in close proximity to each other, and linishing an area of said samples across a surface parallel or tangential to said surface of the backing member.

In the present specification it will be appreciated that the term "linishing", which means grinding with an abrasive medium, for example belt grinding is intended to include equivalent surfacing operations suitable for preparing a surface for subsequent analysis.

In one form of the invention, the samples are held in contact with the backing member by pressing or rolling the samples to embed same into the surface of the backing member whereupon the samples are linished.

In another form of the invention, the samples are firmly held in contact with a linished surface of the backing member by means of clamps whereupon the samples are linished parallel to said linished surface.

In yet another form of the invention, a wire sample is wound around a cylindrical or curved backing member, pressed to give a flattened surface and then linished across the face tangential to the backing member.

In order that the invention may be clearly understood, several different forms are described in more detail below as applied to wire for subsequent analysis by OES or XRF.

Figure 1:
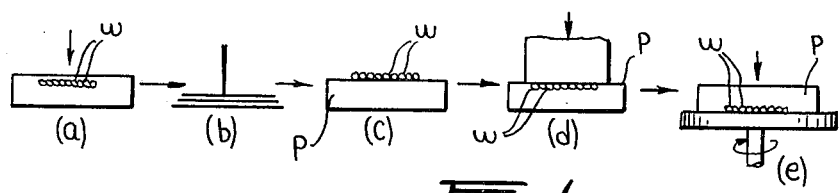
FIG. 1 shows schematically the steps in the preparation method according to a first embodiment.

In the first form of the invention shown schematically in FIG. 1, wire samples W are cleaned of scale and coatings by known mechanical or chemical means (step (a)). The wire W is then cut into lengths suitable for pressing (normally 10–25 mm (step (b)) and placed in close parallel proximity onto a freshly linished mild steel backing plate P (step (c)) (normally 50 × 25 × 4 mm).

To achieve a suitable presentation area with a 15 mm diameter for subsequent analysis by OES a wire of 1 mm diameter requires about 10 lengths whilst a wire 3mm diameter requires only 3. The larger presentation area with a 25 mm diameter demanded by XRF requires proportionally greater numbers of wire lengths. After alignment the wires are subjected to a pressing or rolling force by any suitable laboratory press (step (d)), whereupon the wires become embedded into the surface of the backing plate. It is not usually necessary to positively hold the wires in position for the pressing operation, but in the case of fine wires it may be desirable to locate the wires on the backing plate by slightly magnetising the wires. This can be achieved by passing the wires over a normal strength magnet.

Figure 2:
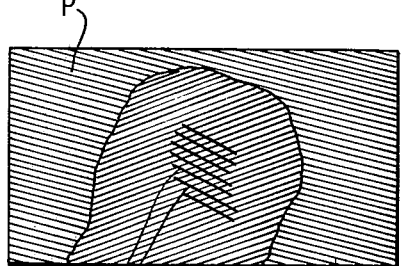
FIG. 2 is an enlarged plan view of the prepared surface showing the wires embedded therein.

The amount of force required depends to a large extent on the sample area required — OES samples can be prepared using a force of about 35 tonnes while XRF samples require forces up to 100 tonnes. The applied force makes the wire and backing plate "flow" in a manner which provides a uniform area of analytical sample cold welded to the backing plate. The resultant surface is then linished smooth suitable for presentation to the analysing instrument (step (e)). FIG. 2 shows a typical sample, in this case 0.8 mm wire W pressed into a mild steel backing plate P, ready for analysis by OES.

For most applications mild steel grade S1021 should suffice as the backing plate, however low carbon grades such as K10A03 and high carbon grades such as WK1068 respectively have found applications for soft and very hard wires respectively. Other metals and alloys should further assist in particular applications e.g. copper or brass for very fine (<0.5mm diam.) soft wires. Further, the invention is not confined to steel samples nor to steel backing plates, e.g. stainless steel, brass, aluminium or tin samples are able to be analysed in an analogous manner.

The backing plates need not necessarily have a smooth polished surface. The plates are preferably linished with a coarse grade abrasive to produce a rough surface and this has been found to provide a better grip after pressing. Alternatively holes may be bored in the backing plate along the length of the sample to achieve greater security of the sample after pressing. This technique is suitable for wires that are softer than the backing plate since the pressing of the wire sometimes causes spreading and lack of penetration. In one arrangement holes may be bored at the ends of the wires so that the pressing operation extrudes the ends of the wire into the holes to thereby achieve more positive retention of the wires to the backing plate. Alternatively, a single hole positioned centrally is suitable for one or more wires, particularly soft wires.

Figure 3:
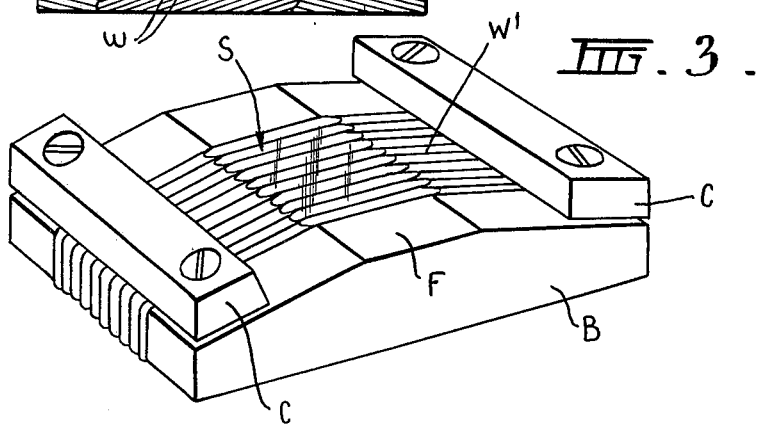
FIG. 3 is a perspective view of an alternative means for achieving sample preparation by a second method.

In the second form of the invention shown in FIG. 3, wire samples W' are arranged on top of a flat surface F and hardened steel bar B and held in place with clamps C. The wires W' are then linished directly as shown or pressed and linished to give the analytical surface S.

Figure 4:
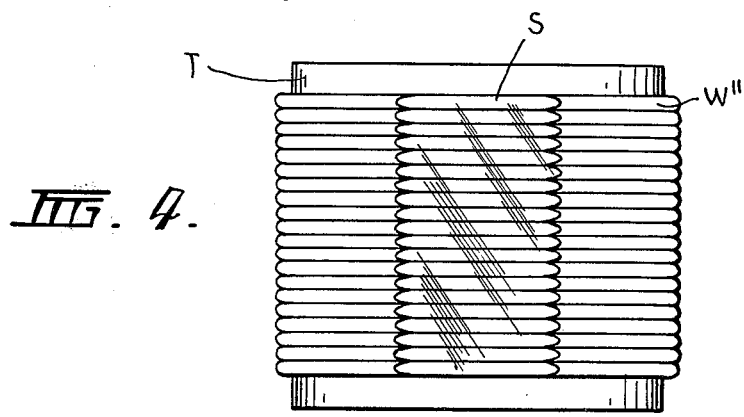
FIG. 4 is a side elevation of another means for achieving sample preparation by a third method.

In the third form shown in FIG. 4, wire W" is wound around a bar or tube T of suitable shape before pressing and linishing to give the analytical surface S. The pressing operation is performed to slightly spread the sample turns to ensure abuttment of adjacent turns.

In both the second and third forms, a longer length of wire is required than for the inlay technique of the first form.

The specific advantages of the techniques described above are as follows:

1. Allows preparation of small samples of steel wire or other metal wire in the size range 0.3 to 12 mm diameter for direct analysis without remelting.

2. The preparation method is suitable for other forms of sample too small for direct analysis, e.g., powder, turnings, millings, tubing, chips and scrapings.

3. The backing plate or tube provides a heat sink for the analysis by OES and other forms of analysis using electric discharge and a single calibration series normally used for large solid samples is applicable to all samples regardless of initial sample size.

4. The presentation of the sample to the spectrometer is superior to the conventional methods since the major axis of the inclusions is in the same plane as the surface.

5. The precision allowed by the preparation is equal to the precision allowed by the preparation of large solid samples. A comparison of OES analysis results performed on bulk samples of the same metal (A(s) and D(s)) and on small wire samples prepared by the first form of the invention is given in Table I below.

6. The preparation method allows the sample to be analysed for any element in the periodic table normally analysed by an instrumental method.

Results obtained using the closely related backing techniques shown in FIG. 3 and 4 were found to be comparable to those obtained using the first technique. The winding of a bobbin is seen to have some applications for fine soft wires.

Results obtained using XRF analysis were also found to be satisfactory.

It is clear from Table 1 that the sample preparation method is eminently suitable for the subsequent performance of instrument analysis.

TABLE 1

| Heat No. | H43765 | | | G3546 | |
|---|---|---|---|---|---|
| Grade | WK22 | | | R 23 | |
| Method of Analysis | A(s) | C(s,x) | | D(s) | C(s,x) |
| Sample No. | | 202 | 209 | | 176 176 |
| Diameter (mm) | | 1.2 | 0.9 | 30 | 6.3 2.0 |
| Condition | — | H.D. | C.C. | — | H.Sw. H.Sw. |
| Element | | | | | |
| %C | 0.10 | 0.10 | 0.10 | 0.20 | 0.21 0.22 |
| Mn | 1.30 | 1.28 | 1.28 | 0.75 | 0.74 0.76 |
| Si | 0.84 | 0.86 | 0.85 | 0.27 | 0.27 0.26 |
| P | 0.024 | 0.022 | 0.022 | 0.036 | 0.034 0.033 |
| S | 0.018 | 0.014 | 0.015 | 0.025 | 0.032 0.031 |

We claim:

1. A method of preparing small metal samples of a size normally too small for direct irradiation and excitation by an instrument for analysis by instrumental techniques, said method comprising the steps of holding a representative plurality of said samples in firm contact with a surface of a backing member, said plurality of said samples held in close proximity to each other and providing an area of said samples upon said surface, and linishing smooth the samples of said area across a surface parallel or tangential to said backing member surface to provide an analytical surface which is suitable for said instrumental analysis.

2. The method of claim 1, including, prior to said linishing step, the steps of placing said samples on said surface in close proximity to each other followed by pressing said samples against said surface with sufficient force to embed and cold weld same in said surface.

3. The method of claim 1, including prior to said linishing step the step of holding said samples firmly in contact with said surface by clamping the ends of the samples to the backing member.

4. The method of claim 1, including the step of winding a plurality of turns of a wire sample around a backing member with said turns abutting each other, and pressing the wire turns against the backing member prior to the linishing step.

5. The method of claim 4, wherein said backing member is cylindrical or curved and said linishing step is performed in a plane tangential to said backing member.

6. The method of claim 1 including the steps of cleaning the samples of scale and coatings by known means and linishing said surface prior to contacting said samples with said surface.

7. The method of claim 6, wherein said surface is linished with a coarse abrasive to assist in retaining samples on said surface.

8. The method of claim 1, comprising the further step of forming holes or pockets in said surface into which at least a portion of said samples are pressed to cause keying of the samples to the backing member.

9. The method of claim 2, wherein the backing member is of mild steel and said pressing operation is performed at between 3 to about 100 tonnes depending on the size of the area required for subsequent analysis.

10. Method of claim 1, wherein said metal samples are of a metal selected from the group consisting of steel, stainless steel, brass, aluminum and tin.

11. Method of claim 1, wherein said backing member is a metallic backing member.

12. Method of claim 1, wherein said samples are wire samples.

13. Method of claim 12, wherein said wire samples are of a size of about 0.3 to about 12 mm in diameter.

* * * * *

UNITED STATES PATENT AND TRADEMARK OFFICE
CERTIFICATE OF CORRECTION

PATENT NO. : 4,120,584
DATED : October 17, 1978
INVENTOR(S) : Raymond John Hodges and Charles Brian Belcher It is certified that error appears in the above-identified patent and that said Letters Patent are hereby corrected as shown below:

Inventor Charles Belcher's address is shown as Birmingham. This should read Birmingham Gardens.

Assignee appears as Australian Wire Industries (Pty.) Limited. This should read Australian Wire Industries Proprietary Limited.

Signed and Sealed this

Twenty-seventh Day of March 1979

[SEAL]

Attest:

RUTH C. MASON
Attesting Officer

DONALD W. BANNER
Commissioner of Patents and Trademarks